United States Patent
Beck et al.

(10) Patent No.: US 6,221,595 B1
(45) Date of Patent: Apr. 24, 2001

(54) **DETECTION OF *MONILINIA* SPP. USING THE POLYMERASE CHAIN REACTION**

(75) Inventors: James Joseph Beck; Christy Violet Perry, both of Cary, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/258,967

(22) Filed: Mar. 1, 1999

(51) Int. Cl.[7] .............................. C12Q 1/68; C12P 19/34; C07H 21/04
(52) U.S. Cl. ........................ 435/6; 435/91.2; 536/23.1; 536/24.3
(58) Field of Search ........................ 435/6, 91.2, 91.5; 536/23.1, 24.3

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 5,426,027 | * 6/1995 | Lott et al. | 435/6 |
| 5,585,238 | 12/1996 | Ligon et al. | 435/6 |
| 5,635,353 | * 6/1997 | Lott et al. | 435/6 |
| 5,780,271 | * 7/1998 | Ristaino et al. | 435/91.2 |
| 5,792,611 | * 8/1998 | Hamelin et al. | 435/6 |

OTHER PUBLICATIONS

Snyder et al., CAN. J. Plant Pathol. vol. 21, No. 1, pp. 70–77, 1999.*
Holst–Jensen et al., "Molecular Phylogeny and Evolution of Monilinia (Sclerotiniaceae) Based on Coding and noncoding rDNA Sequences" American Journal of Botany 84(5): 686–701, May 1997.*
Fulton and Brown, Use of SSU rDNA group–I intron to distinguish Monilinia fructicola from M. laxa and M. fructigena, FEMS Microbiology Letters, 157:307–312 (1997).
Holst–Jensen et al., Molecular Phylogeny and Evolution of Monilinia (Sclerotiniaceae) Based on Coding and Noncoding RDNA Sequences, American Journal of Botany, 84(5):686–701 (1997).
Holst–Jensen et al., Mycologia 89:885–899 (1997).
Snyder et al., Genbank accession AFD10503 (Aug. 3, 1997).
Snyder et al., Genbank accession AF10504 (Aug. 3, 1997).
Compendium of Stone Fruit Diseases, Amer. Phytopath. Soc. pp. 7–10, 1995.
Fulton and Brown, Use of SSU rDNA group–I intron to distinguish *Monilinia fructicola* from *M. laxa* and *M. fructigena*, FEMS Microbiology Letters, 157:307–312 (1997).
James, 1981; Seed Sci. & Technol. 9: 679–685.
Jensen et al., Molecular Phylogeny and Evolution of Monilinia (Sclerotiniaceae) Based on Coding and Noncoding RDNA Sequences, American Journal of Botany, 84(5):686–701 (1997).
Johanson and Jeger 1993; Mycol. Res. 97:670–674.
Lee and Taylor (1990; In: PCR Protocols: A Guide to Methods and Applications; Eds.: Innes et al.; pp. 282–287.
Lee et al. (1990) Fungal Genetics Newsletter 35:23–24.
Nazar et al. 1991; Physiol. and Molec. Plant Pathol. 39: 1–11.
Raeder & Broda (1985) Letters in Applied Microbiology 2:17–20.
Schesser et al. 1991, Applied and Environ. Microbiol. 57:553–556.
White et al., 1990; In: PCR Protocols; Eds.: Innes et al.; pp. 315–322.

* cited by examiner

*Primary Examiner*—W. Gary Jones
*Assistant Examiner*—Jehanne Souaya
(74) *Attorney, Agent, or Firm*—J. Timothy Meigs

(57) ABSTRACT

The present invention relates to the use of primers in polymerase chain reaction assays for the detection of fungal pathogens, particularly *Monilinia laxa* and *Monilinia fructicola*. Specific primers are identified as being useful for the indentification of fungal isolates, particularly *Monilinia laxa* and *Monilinia fructicola*, using PCR based techniques.

12 Claims, No Drawings

US 6,221,595 B1

DETECTION OF *MONILINIA* SPP. USING THE POLYMERASE CHAIN REACTION

FIELD OF THE INVENTION

The present invention relates to the use of primers in polymerase chain reaction assays for the detection of *Monilinia laxa* and *Monilinia fructicola*. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; *Proc. 1981 Brit. Crop Prot. Conf.*) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford; Cereal Diseases, John Wiley, 1983).

Brown rot is a major, global disease of commercially grown Prunus species (1995; Compendium of Stone Fruit Diseases, Amer. Phytopath. Soc. Pp 7–10). Brown rot, depending on the geographical region, can be caused by *Monilinia laxa, M. fructicola* and *M. fructigena*. *M. fructigena* has not been detected in North America, whereas *M. fructicola* has not been found in Europe. *M. fructigena* has been detected on pome and stone fruits in Europe, but *M. laxa* is responsible for the most significant crop damage. Brown can produce financial losses directly from crop loss due to blossom and twig blight and fruit rot in addition to fungicide expense.

In view of the above, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides Internal Transcribed Spacer (ITS) DNA sequences that show variability between different fungal pathotypes. Such DNA sequences are useful in the method of the invention as they can be used to derive primers for use in polymerase chain reaction (PCR)-based diagnostic assays. These primers generate unique fragments in PCR reaction in which the DNA template is provided by specific fungal pathotypes and can thus be used to identify the presence or absence of specific pathotypes in host plant material before the onset of disease symptoms.

In a preferred embodiment, the invention provides ITS-derived diagnostic primers for the detection of *Monilinia laxa*. In an additional preferred embodiment, the invention provides ITS-derived diagnostic primers for the detection of both *M. laxa* and *M. fructicola*.

This invention provides the possibility of assessing potential damage in a specific crop variety-pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase.

Kits useful in the practice of the invention are also provided. The kits find particular use in the identification of the fungal pathogens *Monilinia laxa* and *Monilinia fructicola*.

BRIEF DESCRIPTION OF THE SEQUENCES IN THE SEQUENCE LISTING

SEQ ID NO:1 Oligonucleotide Primer ITS1.
SEQ ID NO:2 Oligonucleotide Primer ITS2.
SEQ ID NO:3 Oligonucleotide Primer ITS3.
SEQ ID NO:4 Oligonucleotide Primer ITS4.
SEQ ID NO:5 Oligonucleotide Primer JB668.
SEQ ID NO:6 Oligonucleotide Primer JB669.
SEQ ID NO:7 Oligonucleotide Primer JB670.
SEQ ID NO:8 Oligonucleotide Primer JB671.
SEQ ID NO:9 Oligonucleotide Primer JB672.
SEQ ID NO:10 Oligonucleotide Primer JB673.
SEQ ID NO:11 Oligonucleotide Primer JB674.

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene regions of particular fungal pathogens as well as primers derived from these regions that are capable of identifying the particular pathogen. These ITS DNA sequences from different pathotypes within a pathogen species or genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57: 553–556), and random amplified polymorphic DNA (i.e. RAPD) markers were able to distinguish numerous races of *Gremmeniella abietina*, the causal agent of scleroderris canker in conifers. U.S. Pat. No. 5,585,238 (herein incorporated by reference in its entirety) describes primers derived from the ITS sequences of the ribosomal RNA gene region of strains of Septoria, Pseudocercosporella, and Mycosphaerella and their use in the identification of these fungal isolates using PCR-based techniques. In addition, U.S. Pat. No. 5,955,274 (herein incorporated by reference in its entirety) describes primers derived from the ITS sequences of the ribosomal RNA gene region of strains of Fusarium and their use in the identification of these fungal isolates using PCR-based techniques. Furthermore, U.S. Pat. No. 5,810,997 (herein incorporated by reference in its entirety) describes primers derived from the ITS sequences of the ribosomal RNA gene region of strains of Cercospora, Helminthosporium, Kabatiella, and Puccinia and their use in the identification of these fungal isolates using PCR-based techniques.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al., 1990; In: PCR Protocols; Eds.: Innes et al; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Sequences of representative oligonucleotide primers derived from ITS sequences are disclosed in SEQ ID NOs: 1–11. The sequences find use in the PCR-based identification of the pathogens of interest.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol.* 57:553–556. See also, Nazar et al. (1991; *Physiol. and Molec. Plant Pathol.* 39:1–11), which used PCR amplification to exploit differences in the ITS regions of *Verticillium albo-atrum* and *Verticillium dahliae* and therefore distinguish between the two species; and Johanson and Jeger (1993; *Mycol. Res.* 97: 670–674), who used similar techniques to distinguish the banana pathogens *Mycosphaerella fijiensis* and *Mycospharella musicola*.

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287.

The published ITS sequences were compared within each pathogen group to locate divergences that might be useful to test in PCR to distinguish the different species and/or strains. From the identification of divergences, numerous primers were synthesized and tested in PCR-amplification. Templates used for PCR-amplification testing were firstly purified pathogen DNA, and subsequently DNA isolated from infected host plant tissue. Thus, it was possible to identify pairs of primers that were diagnostic, i.e. that identified one particular pathogen species or strain but not another species or strain of the same pathogen. Primers were also designed to regions highly conserved among the species to develop genus-specific primers as well as primers that will identify any of several fungal pathogens that cause a particular disease. For example, primers were developed to detect both *M. laxa* and *M. fructicola*.

Preferred primer combinations are able to distinguish between the different species or strains in infected host tissue, i.e. host tissue that has previously been infected with a specific pathogen species or strain. This invention provides numerous primer combinations that fulfill this criterion for *M. laxa* and *M. fructicola*. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree ° C. to achieve good sensitivity and should be void of significant secondary structure and 3' overlaps between primer combinations. Primers generally have sequence identity with at least about 5–10 contiguous nucleotide bases of ITS1 or ITS2. In preferred embodiments, primers are anywhere from approximately 5–30 nucleotide bases long.

The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1
Fungal Isolates and Genomic Fungal DNA Extraction

See Table 1 for a listing of the fungal isolates used and their source. Fungi are grown in 150 ml potato dextrose broth inoculated with mycelial fragments from PDA (Potato Dextrose Agar) cultures. Cultures are incubated on an orbital shaker at 28° C. for 7–11 days. Alternatively, mycelia is isolated directly from a PDA plate. Mycelia are pelleted by centrifugation and then ground in liquid nitrogen, and total genomic DNA is extracted using the protocol of Lee and Taylor (1990; In: *PCR Protocols: A Guide to Methods and Applications*; Eds.: Innes et al.; pages 282–287).

tissue. Macerate the tissue using a Bioreba Homex 6 homogenizer set at 70. Grind the tissue until fibrous.
(3) Aliquot the extraction juice into eppendorf tubes on ice.
  (a) Boil the concentrated extract for 5 minutes.
  (b) Place the boiled extract on ice. Microfuge the boiled extract for 5 minutes.
  (c) Make 1:2, 1:5, 1:10, 1:20 and 1:50 dilutions of the supernatant from the microfuged extract in $dH_2O$.
  (d) Store the diluted extracts on ice until ready to use.

Example 3
Polymerase Chain Reaction Amplification

Polymerase chain reactions are performed with the Gene-Amp Kit from Perkin-Elmer/Cetus (Norwalk, Conn.; part no. N808-0009) using 50 mM KCl, 2.5 mM $MgCl_2$, 10 mM Tris-HCl, pH8.3, containing 200 µM of each dTTP, dATP, dCTP, and dGTP, 50 pmol each primer, 2.5 units of Taq polymerase and 10 ng of genomic DNA or 1 µl of diluted almond extract in a final volume of 50 µl. Reactions are run for 30–40 cycles of 15 s at 94° C., 15 s at 50° C.–70° C., and 45 s at 72° C. in a Perkin-Elmer Model 9600 or 9700 thermal cycler. The products are analyzed by loading 10 µl of each PCR sample on a 1.0% agarose gel and electrophoresing.

Example 4
Synthesis and Purification of Oligonucleotides

Oligonucleotides (primers) are synthesized by, for example, either Integrated DNA Technologies (Coralville, Iowa) or Midland Certified Reagent Company (Midland, Tex.).

TABLE 1

Source of Test Isolates

| Isolate | Organism | Source | Isolation | Origin |
| --- | --- | --- | --- | --- |
| 26255 | *Colletotrichum acutatum* | ATCC[1] | tomato | New Zealand |
| 66367 | *Colletotrichum acutatum* | ATCC[1] | strawberry | Indiana |
| 60468 | *Colletotrichum acutatum* | ATCC[1] | *Vaccinium corymbosum* | New Zealand |
| 42373 | *Colletotrichum acutatum* | ATCC[1] | mango | Australia |
| 38689 | *Colletotrichum acutatum* f. sp. *pinea* | ATCC[1] | *Pinus radiata* | — |
| 12117 | *Cladosporium carpophilum* | ATCC[1] | peach | Wisconsin |
| 46762 | *Sclerotinia sclerotiorum* | ATCC[1] | cauliflower | Australia |
| 26261 | *Colletotrichum gloeosporioides* | ATCC[1] | oranges | — |
| 38237 | *Colletotrichum gloeosporioides* | ATCC[1] | mango | — |
| 44228 | *Colletotrichum gloeosporioides* | ATCC[1] | *Stylosanthes hamata* | Australia |
| 66106 | *Monilinia laxa* | ATCC[1] | apricot | Spain |
| 32671 | *Monilinia laxa* | ATCC[1] | Nectarine | California |
| 9953 | *Monilinia laxa* | ATCC[1] | Rotted fruit | — |
| 32670 | *Monilinia fructicola* | ATCC[1] | Peach | California |
| 46607 | *Monilinia fructicola* | ATCC[1] | peach | Washington |
| 42248 | *Monilinia fructicola* | ATCC[1] | peach | New Zealand |
| BC29 | *Botrytis cinera* | Novartis[2] | — | — |

[1]American Type Culture Collection, Rockville, Maryland, USA
[2]Novartis Crop Protection, Research Triangle Park, North Carolina, USA Example 2
DNA Extraction from Almond tissues
DNA is extracted from almond plant parts as follows:
Bulk Maceration Method:
(1) Almond blossoms or almond halves were placed in a Bioreba (Reinach, Switzerland) heavy duty plastic bag (cat#490100). Weigh the plant tissue, plastic bag with leaves minus the tare (weight of the plastic bag).
(2) Add an equal volume (ml) of Muller Extraction Buffer (0.1% w/v Tween-80; 0.04 M Tris-Cl, pH 7.7; 0.15 M NaCl; 0.1% w/v BSA-Pentex fraction V; 0.01% w/v sodium azide; 200 mM EDTA) per weight (g) of wheat Example 5
Selection of Species-Specific Primers A multiple sequence alignment is made of *M. laxa* and *M. fructicola* ITS region sequences from GenBank (National Center for Biotechnology Information, Bethesda, Md.) listings: AF010500, AF010503, AF010504, Z73777 and Z73784. A second alignment is made with *M. laxa* (Z73784), *M. fructicola* (Z73777), *S. sclerotiorum* (Z73799) and *B. cinera* (U21817). Oligonucleotide primers such as those shown below in Table 2 are synthesized according to Example 4 based on analysis of the aligned sequences. Primers are designed to the regions that contain the greatest differences in sequence among the fungal species. Primers are also designed to regions highly conserved among the two Monilinia species in attempt to develop genus-specific primers.

In addition, the published ribosomal gene-specific primers ITS1, ITS2, ITS3 and ITS4 (White et al., 1990; In: PCR Protocols; Eds.: Innes et al. pages 315–322) are synthesized for testing in combination with the primers specific for the ITS regions.

assayed as described in Example 3 using the diagnostic primers. Other fungal DNA species and isolates are tested for the ability of the diagnostic primers to cross-react therewith. The results of representative experiments are as follows:

M. laxa/M. fructicola-specific primer combination JB669 (SEQ ID NO: 6) and JB670 (SEQ ID NO: 7) amplified a 256 bp fragment from DNA from all of the M. laxa and M.

TABLE 2

Primers Designed for Fungal Detection

| Primer Template | Primer | Primer Sequence | |
|---|---|---|---|
| 18S rDNA | ITS1 | 5'TCCGTAGGTGAACCTGCGG3' | (SEQ ID NO:1) |
| 5.8S rDNA | ITS2 | 5'GCTGCGTTCTTCATCGATGC3' | (SEQ ID NO:2) |
| 5.8S rDNA | ITS3 | 5'GCATCGATGAAGAACGCAGC3' | (SEQ ID NO:3) |
| 25S rDNA | ITS4 | 5'TCCTCCGCTTATTGATATGC3' | (SEQ ID NO:4) |
| M. fructicola | JB668 | 5'GTATGCTCGCCAGAGGATAAT3' | (SEQ ID NO:5) |
| M. laxa | JB669 | 5'GTATGCTCGCCAGAGAATAAT3' | (SEQ ID NO:6) |
| M. laxa/M. fructicola | JB670 | 5'ATAGACTCAATACCAAGCTGT3' | (SEQ ID NO:7) |
| M. fructicola | JB671 | 5'TATGCTCGCCAGAGGATAATT3' | (SEQ ID NO:8) |
| M. laxa | JB672 | 5'TATGCTCGCCAGAGAATAATC3' | (SEQ ID NO:9) |
| M. fructicola | JB673 | 5'GGTTTTGGCAGAAGCACACT3' | (SEQ ID NO:10) |
| M. laxa | JB674 | 5'GTTTTGGCAGAAGCACACC3' | (SEQ ID NO:11) |

Example 6
Determination of Primer Specificity to Purified Fungal Genomic DNA

PCRs are performed according to Example 3 using different primer combinations (Table 3) in an attempt to amplify single specific fragments. Specific PCR amplification products are produced from primers designed from the ITS regions between the small and large ribosomal DNA subunits of each fungal strain of interest.

fructicola isolates listed in Table 1 and from Monilinia spp.-infected almond tissue. This primer combination did not amplify a diagnostic fragment from healthy almond tissue nor from purified genomic DNA from the following common almond pathogens listed in Table 1: C. acutatum, C. carpophilum, S. sclerotiorum, C. gloeosporioides and B. cinera. Similar diagnostic results were obtained with the following M. laxa/M. fructicola-specific primer combinations: JB669 (SEQ ID NO:6) and ITS4 (SEQ ID NO:4),

TABLE 3

ITS-Derived Diagnostic PCR Primers

| Primer Specificity | 5' Primer | 3' Primer | Approximate size of amplified fragment |
|---|---|---|---|
| M. laxa/M. fructicola | JB669 (SEQ ID NO: 6) | ITS4 (SEQ ID NO: 4) | 433 bp |
| M. laxa | JB672 (SEQ ID NO: 9) | ITS4 (SEQ ID NO: 4) | 473 bp |
| M. laxa/M. fructicola | JB668 (SEQ ID NO: 5) | ITS4 (SEQ ID NO: 4) | 498 bp |
| M. laxa/M. fructicola | JB669 (SEQ ID NO: 6) | JB670 (SEQ ID NO: 7) | 448 bp |
| M. laxa | JB672 (SEQ ID NO: 9) | JB670 (SEQ ID NO: 7) | 438 bp |
| M. laxa/M. fructicola | JB668 (SEQ ID NO: 5) | JB670 (SEQ ID NO: 7) | 357 bp |
| M. laxa/M. fructicola | ITS1 (SEQ ID NO: 1) | JB670 (SEQ ID NO: 7) | 512 bp |

Example 7
Determination of Primer Specificity to Plant Tissue Infected with Fungi and Cross-Reactivity with Other Fungal Pathogens Total genomic DNA is isolated as described in Example 2 from visibly infected and uninfected parts of the almond tree. PCRs are performed as described in Example 3 testing primer combinations such as those listed in Table 3 against DNA from the almond tissue. Purified fungal genomic DNAs are obtained as described in Example 1 and PCR JB668 (SEQ ID NO:5) and ITS4 (SEQ ID NO:4), ITS1 (SEQ ID NO:1) and JB670 (SEQ ID NO:7), JB668 (SEQ ID NO:5) and JB670 (SEQ ID NO:7).

The primers JB672 (SEQ ID NO:9) and JB670 (SEQ ID NO:7) amplified a 255 bp fragment from DNA from M. laxa isolates #32671, #66106 and #9953. These primers did not amplify from purified genomic DNA from the following common almond pathogens listed in table 1: M. fructicola, C. acutatum, C. carpophilum, S. sclerotiorum, C. gloeosporioides and B. cinera. Similar diagnosis results were obtained with the *M. laxa* specific primer combination JB672 (SEQ ID NO:9) and ITS4 (SEQ ID NO:4).

While the present invention has been described with reference to specific embodiments thereof, it will be appreciated that numerous variations, modifications, and further embodiments are possible, and accordingly, all such variations, modifications and embodiments are to be regarded as being within the scope of the present invention.

---

What is claimed is:

1. An oligonucleotide primer for detection of Monolinia spp. using the polymerase chain reaction, wherein said primer is selected from the group consisting of SEQ ID NO:5, SEQ ID NO:6, SEQ ID NO:7, and SEQ ID NO:9.

2. A pair of oligonucleotide primers for detection of Monolinia spp. using the polymerase chain reaction, wherein at least one of said primers is an oligonucleotide primer selected from the group consisting of SEQ ID NO:5, SEQ ID NO:6, SEQ ID NO:7, and SEQ ID NO:9.

3. The pair of oligonucleotide primers of claim 2, wherein one of said primers is selected from the group consisting of SEQ ID NO:5, SEQ ID NO:6, SEQ ID NO:7, and SEQ ID NO:9, and wherein the other of said primers is selected from the group consisting of SEQ ID NOs: 1–4.

4. A pair of oligonucleotide primers for detection of Monolinia spp. using the polymerase chain reaction, wherein said pair of primers is selected from the group consisting of:

SEQ ID NO:6 and SEQ ID NO:7;
SEQ ID NO:6 and SEQ ID NO:4;
SEQ ID NO:5 and SEQ ID NO:4;
SEQ ID NO:5 and SEQ ID NO:7;
SEQ ID NO:1 and SEQ ID NO:7
SEQ ID NO:9 and SEQ ID NO:7; and
SEQ ID NO:9 and SEQ ID NO:4.

5. A pair of oligonucleotide primers according to claim 4, wherein said pair of primers is used to detect *Monilinia laxa* or *Monilinia fructicola*, and wherein said pair of primers is selected from the group consisting of:

SEQ ID NO:6 and SEQ ID NO:7;
SEQ ID NO:6 and SEQ ID NO:4;
SEQ ID NO:5 and SEQ ID NO:4;
SEQ ID NO:5 and SEQ ID NO:7; and
SEQ ID NO:1 and SEQ ID NO:7.

6. A pair of oligonucleotide primers according to claim 4, wherein said pair of primers is used to detect *Monilinia laxa*, and wherein said pair of primers is selected from the group consisting of: SEQ ID NO:9 and SEQ ID NO:7; and SEQ ID NO:9 and SEQ ID NO:4.

7. A method for the detection of Monolinia spp., comprising the steps of:
(a) isolating DNA from plant tissue infected with Monolinia spp.;
(b) subjecting said DNA to polymerase chain reaction amplification using at least one primer according to claim 1; and
(c) detecting Monolinia spp. by visualizing the product or products of said polymerase chain reaction amplification.

8. The method of claim 7, wherein the Monolinia spp. is *Monilinia laxa* or *Monilinia fructicola*.

9. A method for the detection of Monolinia spp., comprising the steps of:
(a) isolating DNA from plant tissue infected with Monolinia spp.;
(b) amplifying a part of the Internal Transcribed Spacer sequence of the Monolinia spp. using said DNA as a template in a polymerase chain reaction with a pair of primers according to claim 4; and
(c) detecting the Monolinia spp. by visualizing the amplified part of the Internal Transcribed Spacer sequence.

10. The method of claim 10, wherein the Monolinia spp. is *Monilinia laxa* or *Monilinia fructicola*.

11. A diagnostic kit for detection of Monolinia spp. using the polymerase chain reaction, comprising the primer of claim 1.

12. A diagnostic kit for detection of Monolinia spp. using the polymerase chain reaction, comprising the pair of primers of claim 2.

* * * * *

SEQUENCE LISTING

```
<160> NUMBER OF SEQ ID NOS: 11

<210> SEQ ID NO: 1
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
tccgtaggtg aacctgcgg                                                  19

<210> SEQ ID NO: 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gctgcgttct tcatcgatgc                                                 20

<210> SEQ ID NO: 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gcatcgatga agaacgcagc                                                 20

<210> SEQ ID NO: 4
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
tcctccgctt attgatatgc                                                 20

<210> SEQ ID NO: 5
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gtatgctcgc cagaggataa t                                               21

<210> SEQ ID NO: 6
<211> LENGTH: 21
<212> TYPE: DNA
```

```
<213> ORGANISM: Artificial Sequence
<220> FEATURE:
<223> OTHER INFORMATION: Description of Artificial Sequence:
      oligonucleotide

<400> SEQUENCE: 6
gtatgctcgc cagagaataa t                                            21

<210> SEQ ID NO: 7
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
atagactcaa taccaagctg t                                            21

<210> SEQ ID NO: 8
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
tatgctcgcc agaggataat t                                            21

<210> SEQ ID NO: 9
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
tatgctcgcc agagaataat c                                            21

<210> SEQ ID NO: 10
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
ggttttggca gaagcacact                                              20

<210> SEQ ID NO: 11
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
gttttggcag aagcacacc                                               19
```